United States Patent
Nilsson et al.

(10) Patent No.: US 6,526,984 B1
(45) Date of Patent: Mar. 4, 2003

(54) BIOCOMPATIBLE MATERIAL FOR IMPLANTS

(75) Inventors: Kenth Nilsson, Akersberga (SE); Johan Lidman, Stockholm (SE); Karin Ljungstrom, Hässelby (SE); Charlotte Kjellman, Stockholm (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/673,815

(22) PCT Filed: Apr. 21, 1999

(86) PCT No.: PCT/SE99/00644
§ 371 (c)(1),
(2), (4) Date: Oct. 20, 2000

(87) PCT Pub. No.: WO99/54266
PCT Pub. Date: Oct. 28, 1999

(30) Foreign Application Priority Data

Apr. 22, 1998 (SE) .............................................. 9801403
Apr. 22, 1998 (SE) .............................................. 9801405

(51) Int. Cl.$^7$ ............................................. A61B 19/00
(52) U.S. Cl. .................... 128/898; 623/23.56; 501/134; 606/76; 252/62.9 R
(58) Field of Search ....................... 128/898; 623/23.56, 623/23.49; 252/62.9 R; 606/76

(56) References Cited

U.S. PATENT DOCUMENTS

| | | |
|---|---|---|
| 2,976,246 A | 3/1961 | Egerton et al. |
| 4,698,318 A | 10/1987 | Vogel et al. |
| 4,895,574 A * | 1/1990 | Rosenberg .................... 623/24 |
| 4,947,854 A | 8/1990 | Rabinowitz et al. |
| 5,684,061 A | 11/1997 | Ohnishi et al. |

FOREIGN PATENT DOCUMENTS

| | | |
|---|---|---|
| EP | 0 542 514 | 5/1993 |
| EP | 0 824 935 | 2/1998 |
| WO | WO 95/19796 | 7/1995 |

OTHER PUBLICATIONS

"Metastable Ferroelectric Sodium Niobate," Dungan et al., J. Amer. Ceram. Soc., vol. 47 (1964), pp. 73–76.

"Polarization of $NaNbO_3$–$KNbO_3$ Ceramic Solid Solutions," Dungan et al., J. Amer. Ceram. Soc., vol. 48 (1965) p. 601.

"Conventionally Sintered ($Na_{0.5}$, $K_{0.5}$)$NbO_3$ with Barium Additions," Ahn et al., J. Amer. Ceram. Soc., vol. 70 (1987) pp. C–18—C–21.

"(K,Na)$NbO_3$ Ferroelectric Films Synthesized by Cathode Sputtering," Margolin et al., Sov. Phys. Tech. Phys. vol. 33, No. 12 (1998), pp. 1435–1438.

"Ferroelectric Potassium Sodium Niobate (K,Na) $NbO_3$ Thin Films Deposited by rf Cathode Sputtering," Margolin et al., J. Tech. Phys. (Aug. 1987).

"Ferroelectric Properties of (K,Na)$NbO_3$, Thick–Films Prepared by Rapid–Quenching," Takahashi et al. Ferroelectrics, vol. 95 (1989) pp. 209–213.

(List continued on next page.)

Primary Examiner—Paul B. Prebilic
Assistant Examiner—William H Matthews
(74) Attorney, Agent, or Firm—Schiff Hardin & Waite

(57) ABSTRACT

A biocompatible medical implant has at least one part thereof composed of ceramic material with the formula $Na_xK_yNbO_3$, wherein $0 \leq x \leq 0.8$, $0.2 \leq y \leq 1$, and $x+y=1$. The ceramic material can be polarized to give the implant spatially varying piezoelectric properties. Signals can be measured from the respective piezoelectric regions of the selectively polarized ceramic material to provide an indication of the degree of fixation of the implant to surrounding tissue.

14 Claims, 4 Drawing Sheets

Exp 1

Exp 2

OTHER PUBLICATIONS

"Bone Bonding Ability of An Apatite–Coated Polymer Produced Using a Biomimetic Method: A Mechanical and Histological Study in vivo," Nagano et al., J. of Biomed. Matls. Res., vol. 31, No. 4, pp. 487–494 (Internet Abstract).

"Self–setting Bioactive and Biodegradable TTCP–DCPD Apatite Cement," Hamanishi et al., J. Biomed. Matls. Res., vol. 32, No. 3, pp. 383–389 (Internet Abstract).

Piezoelectric Properties of Single Crystal Berlinite, Ozimek et al. 1979 IEEE Int. Frequency Control Symposium, Index 1–33–80 (Internet Abstract).

"The Elastic Dielectric and Piezoelectric Constants of Berlinite," Bailey et al., 1982 IEEE Int. Frequency Control Symposium, Index 1–36–124 (Internet Abstract).

"Isostatically Hot–Pressed Sodium–Potassium Niobate Transducer Material for Ultrasonic Devices," Egerton et al. Amer. Ceram. Soc. Bulletin, vol. 47 (1968) pp. 1151–1156.

"Piezoelectric and Dielectric Properties of Ceramics in the System Potassium–Sodium Niobate," Egerton et al., J. Amer. Ceram. Soc., vol. 42 (1959), pp. 438–442.

"Hot Pressing of Potassium–Sodium Niobates," Jaeger et al., J. Amer. Ceram. Soc., vol. 45 (1962), pp. 207–213.

* cited by examiner

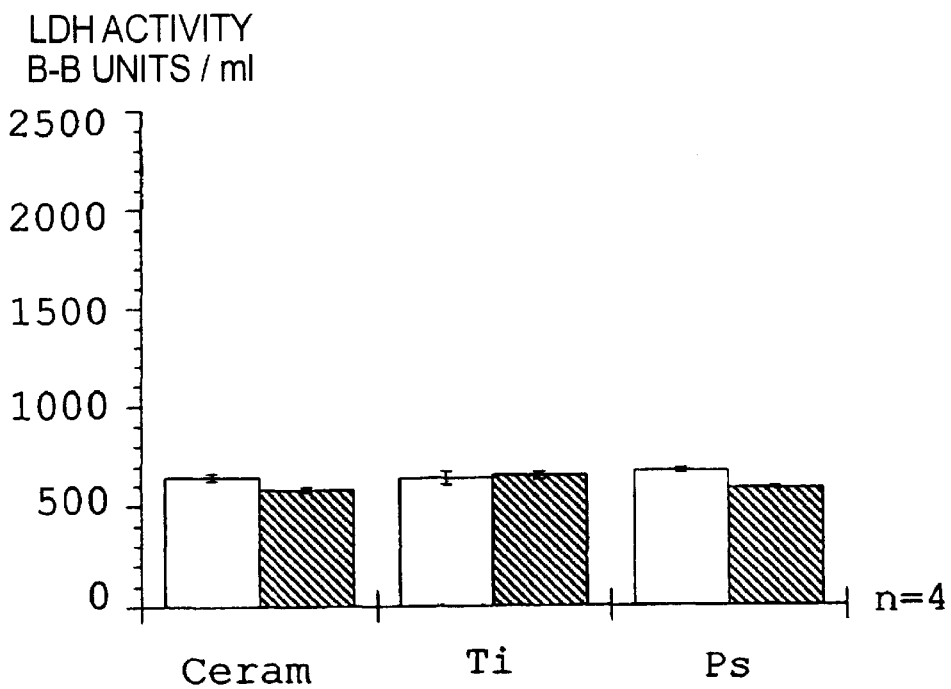
FIG. 1A Exp 1
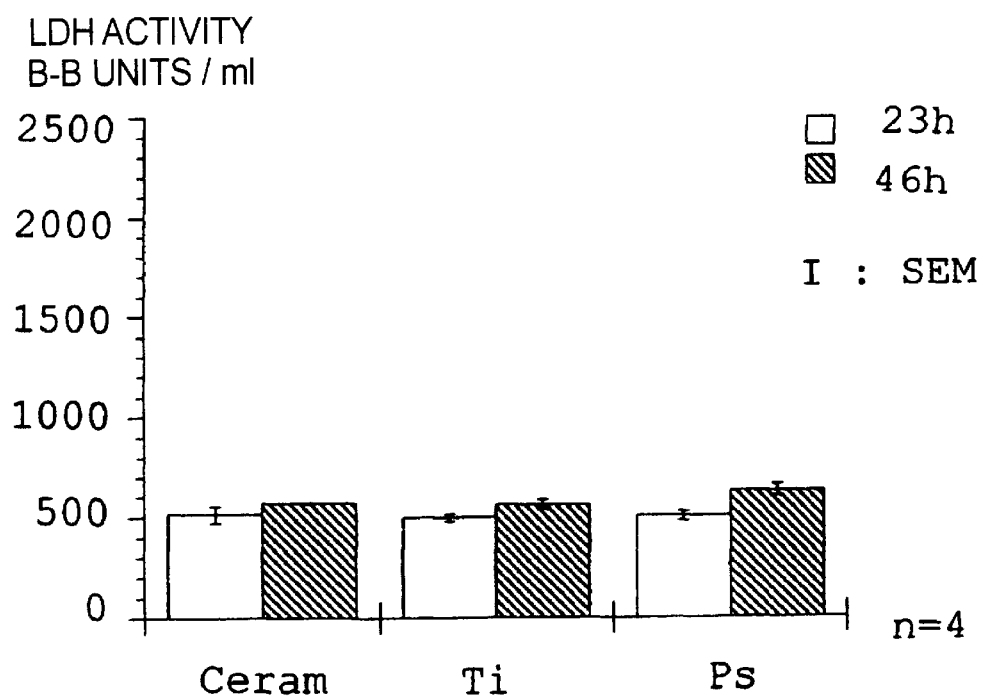
FIG. 1B Exp 2

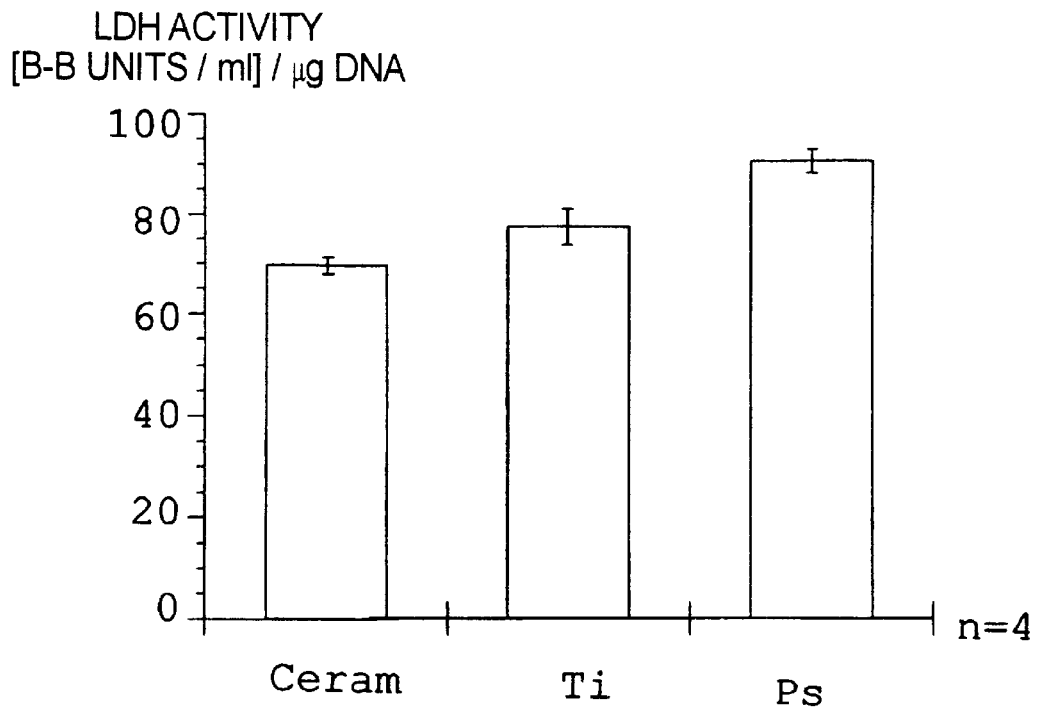
Exp 1     *FIG. 3A*
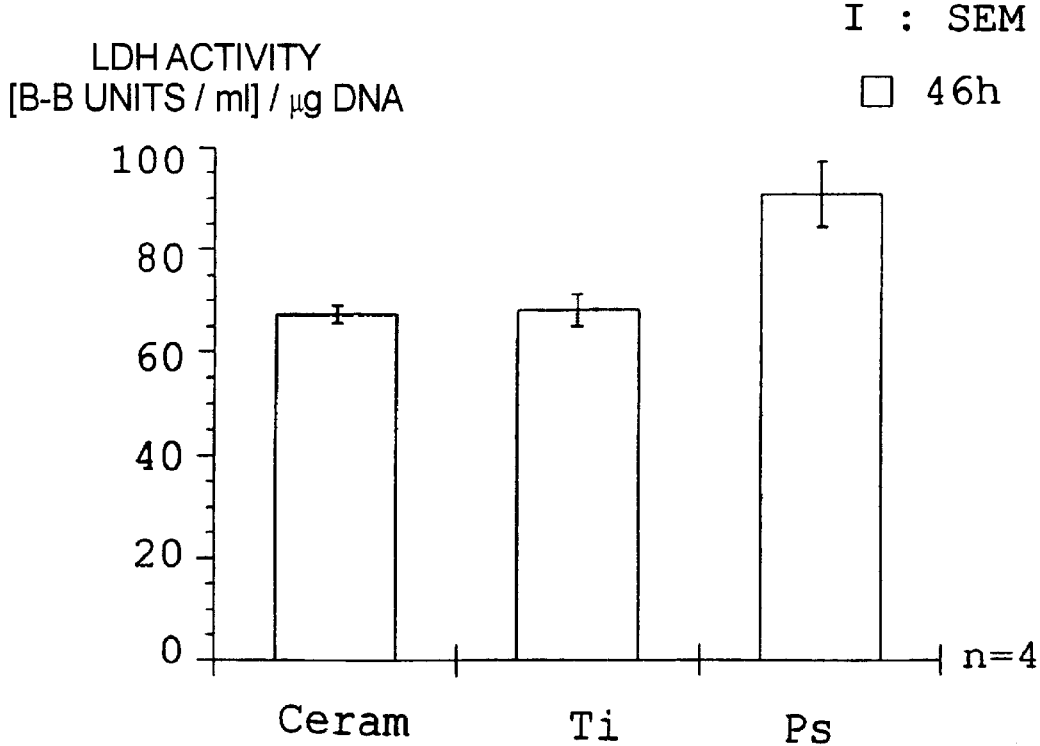
Exp 2     *FIG. 3B*

BIOCOMPATIBLE MATERIAL FOR IMPLANTS

BACKGROUND OF THE INVENTION

1. Field of the Invention

The present invention relates to biocompatible materials for medical implants, and particularly to tissue ingrowth-enhancing biocompatible materials.

2. Description of the Prior Art

The most commonly used rigid biocompatible implant materials are ceramic materials that may be used as bulk materials as for instance $Al_2O_3$. They also may be materials normally found as or used as layers on substrates, such as $TiO_2$, TiN (materials that are considered to be ceramic in nature) or hydroxylapatite. These materials normally are not piezoelectric and normally cannot be polarized so as to become piezoelectric.

Ceramics having mechanical properties comparable to the above ceramic materials and having good piezoelectric properties, i. e. mainly polarizable ceramic ferroelectrics, normally contain components that can be suspected to be potentially harmful in the implanted state, for instance lead, as for instance in lead titanate, lead metaniobate or lead zirconate. It thus is undesirable that these materials directly or indirectly come into contact with body tissue or fluids. This is particularly important for piezo materials that are to be left in the body for a very long time.

Biocompatible phosphate glass ceramics that may contain crystal phases of apatite and $AlPO_4$ in the tridymite and/or berlinite form are disclosed in U.S. Pat. No. 4,698,318. Berlinite is an isotype to quartz and has inherent piezoelectric properties. It is suggested that the piezoelectric properties of the berlinite can be utilized to promote healing of bone fractures. Berlinite has relatively weak piezoelectric properties. Since berlinite only is a part of the material, the overall piezoelectric properties of this material are weak. The piezoelectric properties are obtained by thermal treatments at relatively high temperatures for long time periods said to cause targeted precipitation of apatite or of apatite and $AlPO_4$-crystals. The long-term stability of the material in the implanted state is not discussed, but hydroxylapatite and apatite are at least to some extent biodegradable.

There are some other biocompatible materials with piezoelectric properties. These materials mostly are relatively soft piezoelectric polymers with inherent piezoelectric properties. Other materials are biocompatible polymers containing inorganic polarizable, ceramic ferroelectric particles such as lead zirconate titanate (PZT) or barium titanate. Such polymeric materials are for instance disclosed in U.S. Pat. No. 5,684,061 where they are used as membranes for enhancing bone regeneration.

These materials have relatively weak piezoelectric properties and have a limited use in view of their relative softness, their potential toxicity and their poor mechanical and chemical strength.

U.S. Pat. No. 2,976,246 describes the production of potassium-sodium niobate ceramics exhibiting piezoelectric properties for use in the manufacture of electromechanical transducers for delay lines. Specific compositions are in the range $K_{0.9}Na_{0.1}(NbO_3)$ to $K_{0.1}Na_{0.9}(NbO_3)$, the formula of the preferred embodiment being $K_{0.1}Na_{0.9}(NbO_3)$.

SUMMARY OF THE INVENTION

An object of the invention is to provide a highly biocompatible material that has a long-term stability in the implanted state and that can be wholly or selectively polarized in order to obtain piezoelectric properties for tissue growth promoting purposes.

It is a further object of the present invention to provide a biocompatible ceramic material for an implant which allows the degree of fixation of the implant tissue to be determined.

Another object of the present invention is to provide a medical implant employing biocompatible ceramic material of the type described above.

These objects are inventively achieved in a biocompatible ceramic material and in a medical implant containing such biocompatible ceramic material, wherein the ceramic material comprises $Na_xK_yNbO_3$, wherein $0 \leq x \leq 0.8$, $0.2 \leq y \leq 1$, and $x+y=1$.

In the implant employing such ceramic material, the ceramic material is provided as a film or a layer on an implant body, or on a part comprised of a material other than the ceramic material. The ceramic material can be selectively polarized so as to provide the implant with spatially varying piezoelectric properties, meaning that the implant at one portion or location of its overall structure has a piezoelectric property or characteristic which differs from a piezoelectric property or characteristic at another location or part of the overall implant structure.

By means of these spatially varying piezoelectric properties, an indication of the magnitude of the forces that are transferred from the implant to the adjoining tissue, when the implant is implanted, can be measured, and this measurement is an indication of the degree of fixation of the implant to the surrounding tissue.

DESCRIPTION OF THE DRAWINGS

FIGS. 1A and 1B illustrate the biocompatibility of the material of the invention by means of the lactate dehydrogenase (LDH) activity in B—B units/ml in a culture medium after 23 hours and 46 hours cultivation of $1 \times 10^6$ human monocytes, on a ceramic surface (Ceram), on a titanium surface (Ti), and on tissue culture polystyrene (ps), for two different donors, respectively.

FIGS. 3A and 3B show the LDH activity in B—B units/ml, normalized by a total amount of DNA in wells after 46 hours cultivation of $1 \times 10^6$ monocytes on the same surfaces as in FIG. 1, for two different donors, respectively.

DESCRIPTION OF THE PREFERRED EMBODIMENTS

In a preferred embodiment of the invention, the material consists of $Na_{0.5}K_{0.5}NbO_3$. This material surprisingly has been found to have excellent properties for the use in implants. In addition to this, it is possible to polarize the material in order to provide it with piezoelectric properties. The material thus combines the following properties:

a very high level of biocompatibility, mechanical and chemical stability expected to be at least ten years, a $d_{33}$ that can exceed 100 pCN$^{-1}$, resistivity that can exceed $10^{12}$ Ωm, Curie temperature >160° C., Additionally, the material will function as desired at a working temperature of 36–41° C., a band width of 0.3–20 Hz.

These properties obviously are well suited for use in the human body. It should be noted that the material according to the invention could be provided with piezoelectrical properties (e.g. the dielectric constant) that are better than the corresponding properties of berlinite by a factor of 100.

The piezo material preferably should have a relative density of at least 97%, a maximum pore size of 4 $\mu$m and a maximum grain size of 4 $\mu$m.

In some applications, other properties might be more desirable than the best piezoelectric properties. For instance, in an implant the porosity of the material might be more important than the optimal piezoelectric properties.

The material may be made as a bulk material by means of the hot isostatic pressing methods using sodium carbonate, potassium carbonate and niobium pentoxide as precursors as defined in the following articles from American Ceramic Society Bulletin: Egerton—Dillon in 42(1959) pp438–442, Jaeger—Egerton in 45(1962) pp209–213 and Egerton—Bieling in 47(1968) pp1151–1156.

The material may also be made in the form of films or layers on substrates by means of cathode sputtering methods as for instance described in Margolin et al, "(K,Na)NbO$_3$ ferroelectric films synthesized by cathode sputtering", Sov. Phys. Tech. Phys. 33(12), December 1988, or by other suitable thin film techniques.

The excellent biocompatible properties of the material are illustrated by the following standard toxicology test.

In this test monocytes were cultured on the surface of (Na,K)NbO$_3$ (Ceram), and on two control surfaces titanium (Ti) and Polystyrene (Ps). The cytoplasmic enzyme lactate dehydrogenase (LDH) is detected extracellularly and is an indicator of the degree of injury inflicted to cells. Measurements of LDH were performed on the cellular medium after 23 h and after 46 h.

Cells can be activated and deteriorated not only by direct material interactions but also by soluble factors, including chemicals released from the material, so therefore the study also examined if there were any bacterial products (endotoxin) present in the culture medium before and after the test.

The result show that human monocytes in terms of viability are not negatively affected during culture up to 46 hours by the presence of (Na,K)NbO$_3$.

Figure 2A:
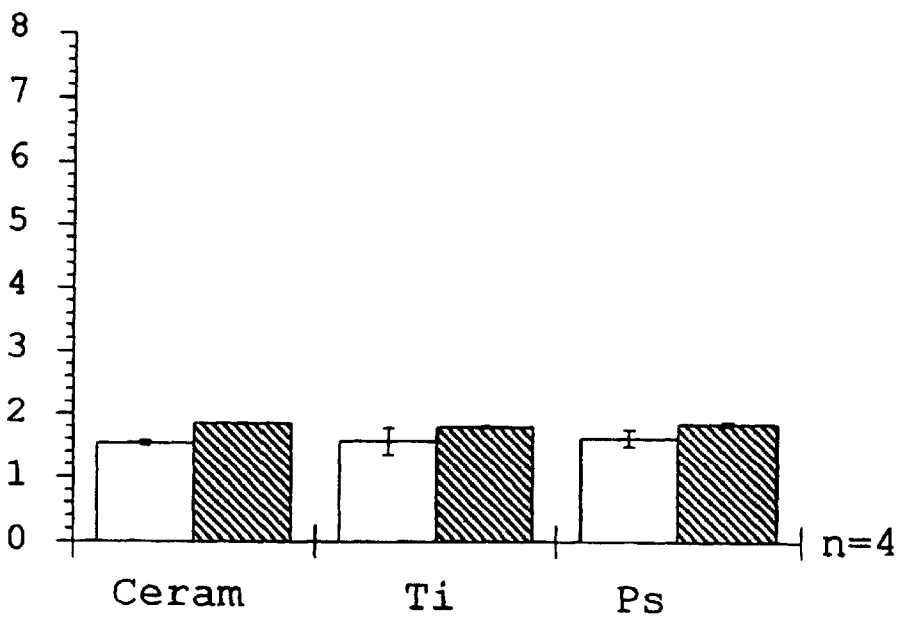
FIGS. 2A and 2B show the LDH activity as $\mu$katal/l, in the culture medium after 23 hours and 46 hours cultivation of $1 \times 10^6$ human monocytes on the same surfaces as in FIG. 1, for two different donors, respectively.
Figure 2B:
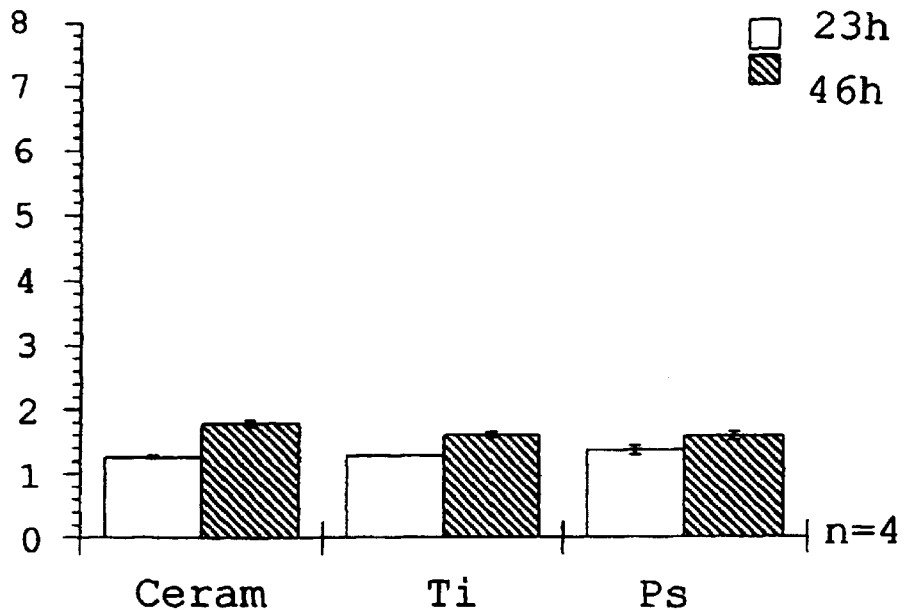
Figure 4:
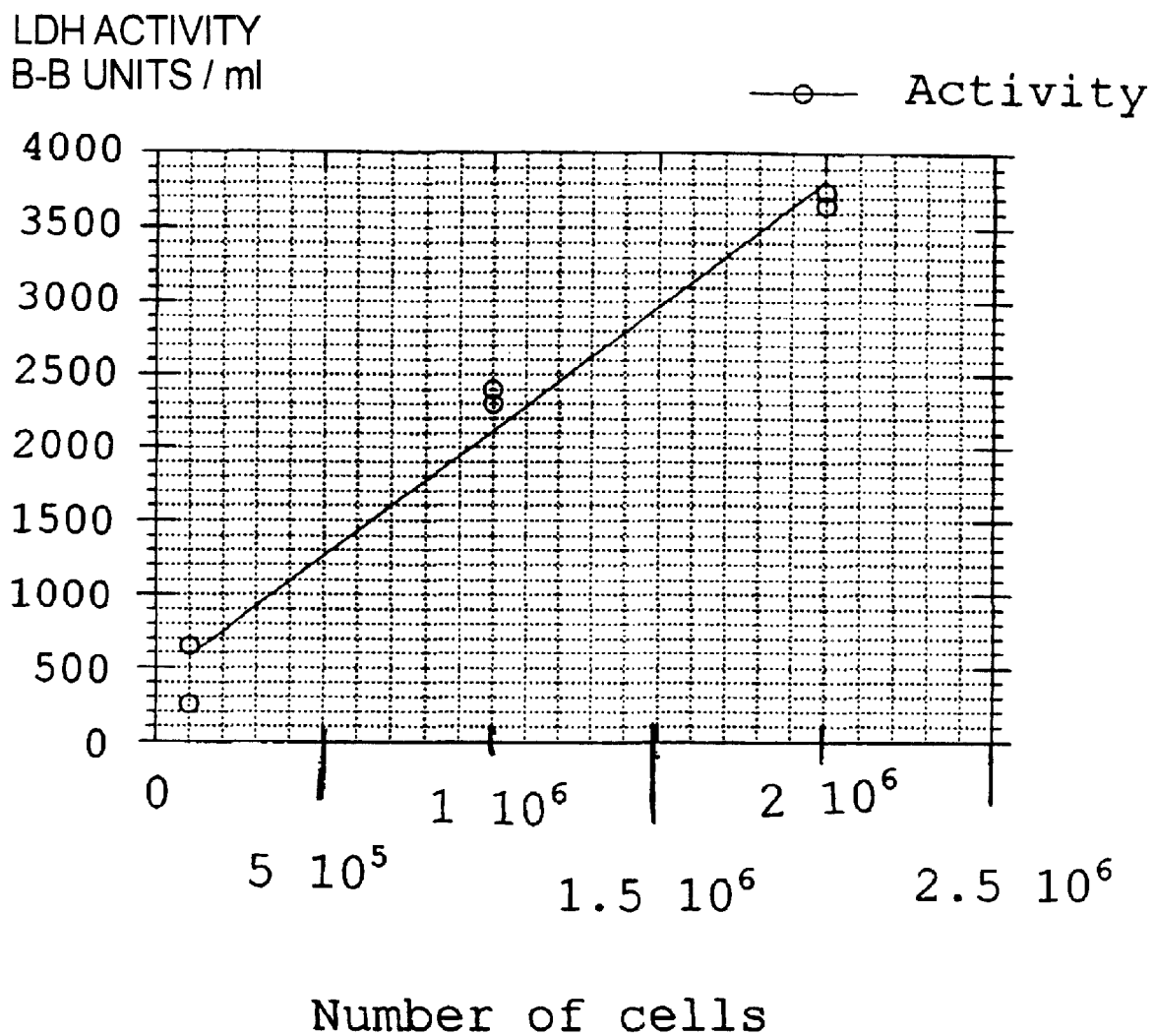
FIG. 4 illustrates the control of LDH activity in B—B units/ml, from dead human monocytes.

FIG. 1A and 1B thus illustrates the biocompatibility of the piezomaterials according to the invention by means of the lactate dehydrogenase (LDH) activity as [B—B units/ml] in the culture medium after 23 and 46 h cultivation of $1\times10^6$ human monocytes, on a ceramic surface (Ceram), on titanium (Ti) and on tissue culture polystyrene (Ps). The cells were from two separate blood donors, exp. 1 respectively exp. 2. The values in the diagram are mean values, the standard error mean (SEM) also being indicated. FIG. 2 shows the LDH activity as $\mu$katal/l, in the culture medium after 23 and 46 h cultivation of $1\times10^6$ human monocytes, on a ceramic surface, titanium and on tissue culture polystyrene. Again cells from two separate blood donors were used, exp. 1 respectively exp. 2. Normal levels in human serum are 8 $\mu$katal/l. The values are mean values±SEM. FIG. 3A and 3B show the LDH activity as [B—B units/ml], normalized by total amount of DNA in wells after 46 h cultivation of $1\times10^6$ human monocytes on a ceramic surface, titanium and on tissue culture polystyrene. Cells from two separate blood donors, exp. 1 respectively exp. 2. The values are mean values±SEM. FIG. 4 illustrates the control of total LDH activity as [B—B units/ml], from dead human monocytes by adding 2% Triton X100 to $1\times10^5$, $1\times10^6$ and $2\times10^6$ human monocytes. The LDH activity between 500 and 700 corresponds approximately to 0.5–1.5$\times10^5$ dead cells.

As is evident from these diagrams, the ceramic material according to the invention has a biocompatibility that closely follows that of titanium. In view of the fact that titanium has proved to be one of the most biocompatible materials and in view of the doubtful biocompatibility of known polarizable ceramic ferroelectrics, this is very unexpected in a ceramic ferroelectric.

Although the test relates to Na$_{0.5}$K$_{0.5}$NbO$_3$, it obviously also is valid for niobates with other proportions of Na and K.

The material according to the invention can be used in several ways in the medical field.

The material as such can be used as a rigid implant material in view of its strength and durability either in bulk form or in the form of films or layers covering other materials.

The material may be polarized in bulk form or in film form in order to achieve piezoelectric properties that can be utilized in order to stimulate the regeneration or growth of the tissue in the vicinity of the material by electric stimulation. In these applications the material also can be used in particulate form in a polymer matrix in view of its excellent biocompatibility since it would not matter if the material directly or indirectly would come into contact with body tissue.

One important advantage of the material according to the invention is that it can be polarized selectively. This means, for instance, that it is possible to obtain implants that have piezoelectric properties in specified locations only and/or have piezoelectric properties varying from weak to strong in dependence on where and to what degree the tissue growth or generation is to be promoted. As with all ceramic ferroelectrics, the piezoelectric properties can be made directional in dependence of the direction of the polarizing field.

Bone implants could for instance be provided with a certain degree of tissue growth promoting capability in one part of the adjoining bone tissue, e.g. the compact bone, and with a different tissue growth promoting capability in another part of the adjoining bone tissue, for instance the cancellous bone. The tissue growth promoting capability alternatively could be matched locally to the local rigidity so as to obtain a constant tissue growth promoting capability along the entire implant surface even if the forces transferred from adjoining tissue varies.

Conversely, the implant material can be used in order to give an indication of the size of the forces transferred from an implant to the adjoining tissue when the implant is implanted. The forces exerted on the piezoelectric material will cause an electrical signal that directly corresponds to the totality of the forces actually acting on the implant. A measurement of this signal can be compared with a theoretical value calculated from the nature of the surrounding tissue, from the geometrical shape of the implant and from the way forces ideally would be transferred from a body with this geometrical shape to a surrounding media. This comparison thus would give an indication whether, and to what extent, the implant actually does engage the adjoining tissue so as to transfer forces.

One use would be the clinical testing of different bone implant designs, for instance dental implant designs. The above comparison would give a value of the actual bone apposition obtained by a specific design.

Since the overall values of the forces transferred are used, the above comparisons only would be mean values, i.e. the comparison would not say anything about the local conditions. A development of this principle thus would be to provide the implant with several separate areas with piezoelectric properties and individually measuring the signal generated from each separate area, thus determining for instance the bone apposition in each separate area. By these means, specific design features of the implant can be evaluated.

The above method could also be used for permanent implants for determining for instance the bone apposition after some time and for following up the long-term fixation of the implant.

One skilled in the art will appreciate that the present invention can be practiced in other ways than by means of the described embodiments, which are presented for purposes of illustration. The present invention is limited only by the claims that follow.

What is claimed is:

1. A method for making a medical implant comprising the steps of:
   providing a medical implant having at least one part adapted for direct contact with tissue; and
   making said at least one part of ceramic material comprising $Na_xK_yNbO_3$, wherein $0 \leq x \leq 0.8$, $0.2 \leq y \leq 1$, and $x+y=1$.

2. A method as claimed in claim 1 wherein $0.2 \leq x \leq 0.8$ and $0.2 \leq y \leq 0.8$.

3. A method as claimed in claim 1 wherein $0.4 \leq x \leq 0.6$ and $0.4 \leq y \leq 0.6$.

4. A method as claimed in claim 1 wherein $x=y=0.5$.

5. A method as claimed in claim 1 comprising making said at least one part of piezoelectric ceramic material having a relative density exceeding 97%.

6. A method as claimed in claim 5 comprising making said at least one part of piezoelectric ceramic material having a pore size of less than 4 $\mu$m.

7. A method as claimed in claim 5 comprising making said at least one part of piezoelectric ceramic material having a grain size of less than 4 $\mu$m.

8. A method as claimed in claim 6 comprising making said at least one part of piezoelectric ceramic material having a piezoelectric constant $D_{33}$ which exceeds 100 $pCN^{-1}$.

9. A method as claimed in claim 1 comprising providing said implant with at least one part comprised of a material other than said ceramic material, and disposing said at least one part of ceramic material as a film on said at least one part composed of a material other than said ceramic material.

10. A method as claimed in claim 9 comprising the additional step of selectively polarizing said film to provide said implant with spatially varying piezoelectric properties.

11. A method as claimed in claim 1 comprising providing said implant with at least one part comprised of a material other than said ceramic material, and disposing said at least one part of ceramic material as a layer on said at least one part composed of a material other than said ceramic material.

12. A method as claimed in claim 11 comprising the additional step of selectively polarizing said layer to provide said implant with spatially varying piezoelectric properties.

13. A method as claimed in claim 1 comprising forming said at least one part of ceramic material as a majority of said implant, and using piezoelectric ceramic material as said ceramic material, and selectively polarizing said piezoelectric ceramic material to provide said implant with spatially varying piezoelectric properties.

14. A method for determining fixation of a medical implant relative to surrounding tissue comprising the steps of:
   implanting a medical implant in a subject having at least a ceramic material part comprising $Na_xK_yNbO_3$, wherein $0 \leq x \leq 0.8$, $0.2 \leq y \leq 1$, and $x+y=1$;
   selectively polarizing said ceramic material part to provide said ceramic material part with spatially varying piezoelectric properties, including respective piezoelectric regions; and
   measuring respective electrical signals from the respective piezoelectric regions caused by interaction of said piezoelectric regions with adjoining tissue, as an indication of a degree of fixation of said implant to said adjoining tissue.

* * * * *